(12) United States Patent
Newton et al.

(10) Patent No.: US 11,097,065 B2
(45) Date of Patent: Aug. 24, 2021

(54) NEEDLE-SHIELD REMOVER

(71) Applicant: Antares Pharma, Inc., Ewing, NJ (US)

(72) Inventors: Ben Newton, Chanhassen, MN (US); Patrick Madsen, Litchfield, MN (US); Kevin Swanson, Plymouth, MN (US)

(73) Assignee: Antares Pharma, Inc., Ewing, NJ (US)

( * ) Notice: Subject to any disclaimer, the term of this patent is extended or adjusted under 35 U.S.C. 154(b) by 196 days.

(21) Appl. No.: 16/311,819

(22) PCT Filed: Jun. 22, 2017

(86) PCT No.: PCT/US2017/038828
§ 371 (c)(1),
(2) Date: Dec. 20, 2018

(87) PCT Pub. No.: WO2017/223354
PCT Pub. Date: Dec. 28, 2017

(65) Prior Publication Data
US 2019/0201634 A1 Jul. 4, 2019

Related U.S. Application Data

(60) Provisional application No. 62/353,496, filed on Jun. 22, 2016.

(51) Int. Cl.
*A61M 5/32* (2006.01)

(52) U.S. Cl.
CPC ............................ *A61M 5/3204* (2013.01)

(58) Field of Classification Search
CPC .... A61M 5/32; A61M 5/3202; A61M 5/3204; A61M 5/31; A61M 5/178
See application file for complete search history.

(56) References Cited

U.S. PATENT DOCUMENTS

| 5,928,205 A | 7/1999 | Marshall |
| 7,771,397 B1 * | 8/2010 | Olson ................. A61M 5/3202 604/192 |
| 7,938,808 B2 | 5/2011 | Pessin |

(Continued)

FOREIGN PATENT DOCUMENTS

| EP | 2361648 A1 | 8/2011 |
| EP | 2923714 A1 | 9/2015 |

(Continued)

OTHER PUBLICATIONS

International Search Report and Written Opinion dated Oct. 12, 2017 for International Patent Application No. PCT/US2017/038828, 11pp.

(Continued)

*Primary Examiner* — Deanna K Hall
(74) *Attorney, Agent, or Firm* — Morgan, Lewis & Bockius LLP

(57) ABSTRACT

An apparatus for removing a needle shield from a syringe may be configured to receive the removable needle shield. The remover may include a body and a deflectable arm. The deflectable arm may include a distal end coupled to the body and a proximate end distal a proximate end of the body. The deflectable arm may be configured to engage and apply a force to the needle shield when the cap is detached from the syringe, thereby removing the needle shield from the syringe.

18 Claims, 14 Drawing Sheets

(56) References Cited

U.S. PATENT DOCUMENTS

| | | | |
|---|---|---|---|
| 7,988,675 B2 | 8/2011 | Gillespie, III et al. | |
| 8,409,138 B2 | 4/2013 | James et al. | |
| 8,512,295 B2 | 8/2013 | Evans et al. | |
| 8,579,866 B2 | 11/2013 | Morgan et al. | |
| 8,591,463 B1 | 11/2013 | Cowe | |
| 8,708,968 B2 | 4/2014 | Julian et al. | |
| 8,747,357 B2 | 6/2014 | Stamp et al. | |
| 8,900,197 B2 | 12/2014 | Crow | |
| 9,199,041 B2 | 12/2015 | Edginton | |
| 9,248,245 B2 | 2/2016 | Ekman et al. | |
| 9,895,493 B2 * | 2/2018 | Burnell | A61M 5/3213 |
| 2013/0035645 A1 | 2/2013 | Bicknell et al. | |
| 2013/0150801 A1 | 6/2013 | Ekman et al. | |
| 2013/0253444 A1 | 9/2013 | Liversidge | |
| 2013/0331796 A1 | 12/2013 | Wozencroft | |
| 2014/0025013 A1 | 1/2014 | Dowds et al. | |
| 2014/0114250 A1 | 4/2014 | DeSalvo et al. | |
| 2014/0288503 A1 * | 9/2014 | Julian | A61M 5/321 604/198 |
| 2014/0343503 A1 | 11/2014 | Holmqvist | |
| 2014/0343505 A1 | 11/2014 | Henley et al. | |
| 2015/0250950 A1 | 9/2015 | Moser et al. | |
| 2016/0015896 A1 | 1/2016 | Cowe et al. | |
| 2016/0015897 A1 | 1/2016 | Swanson et al. | |
| 2017/0361030 A1 * | 12/2017 | Moore | A61M 5/3213 |

FOREIGN PATENT DOCUMENTS

| | | |
|---|---|---|
| JP | 2005-512637 | 5/2005 |
| JP | 2013519474 | 5/2013 |
| JP | 2014-530083 | 11/2014 |
| JP | 2016-508807 | 3/2016 |
| WO | 03051423 A2 | 6/2003 |
| WO | 2013058697 A1 | 4/2013 |
| WO | 2014045336 A1 | 3/2014 |
| WO | 2014060216 A1 | 4/2014 |
| WO | 2014091153 A1 | 6/2014 |
| WO | 2015044561 A1 | 4/2015 |
| WO | 20150044561 A1 | 4/2015 |
| WO | 2015078866 A1 | 6/2015 |
| WO | 2015078867 A1 | 6/2015 |
| WO | 2015078868 A1 | 6/2015 |
| WO | 2015078869 A1 | 6/2015 |
| WO | 2015091850 A1 | 6/2015 |
| WO | 2015144871 A1 | 10/2015 |

OTHER PUBLICATIONS

Office Action dated Jun. 9, 2020 for Canadian Patent Application No. 3027922, 4 pages.

Japanese Office Action for Japanese Patent Application No. 2018-566569, 6 pages.

Japanese Office Action for Japanese Patent Application No. 2018-566569 dated Nov. 26, 2019, 7 pages.

Canadian Office Action dated Nov. 8, 2019 for Canadian Application No. 3,027,992, 5 pages.

Extended European Search Report dated Jan. 23, 2020 for European Patent Application No. 17816233.5, 7 pages.

* cited by examiner

NEEDLE-SHIELD REMOVER

CROSS-REFERENCE TO RELATED APPLICATIONS

This application is a U.S. National Stage filing of International Patent Application No. PCT/US2017/038828 filed Jun. 22, 2017, which claims the benefit of U.S. Provisional Patent Application No. 62/353,496 filed Jun. 22, 2016 entitled "Needle-Shield Remover", each of which is incorporated by reference herein in its entirety.

FIELD OF THE INVENTION

The present application generally relates to syringe needle shield removers and more particularly, to a device for removing a needle shield from a syringe.

BACKGROUND OF THE INVENTION

Needle shields are often used with syringes to prevent accidental needle sticks as well as avoid damage or contamination of the needle tip. The needle shields are typically removable by a user who grasps the syringe in one hand and the needle shield in the other. The user pulls the needle shield away from the syringe to expose the needle tip prior to using the syringe. However, the user's hands may recoil after removing the shield and cause an inadvertent needle stick or damage of the needle if the shield contacts the needle. It may not be possible for a user to grasp the needle shield when an injector device is used which obstructs access to the syringe and needle shield prior to using the injector.

Typical injectors house a syringe and provide a mechanism for exposing the needle in an injection configuration wherein medicament can be transferred from the syringe into a patient. Needle shields may also be provided to cover the tip of needle before and during the syringe insertion into the injector. Injectors usually include a cap to prevent the injector from moving to the injection configuration before the user is ready to inject the medicament. For syringes that require removal of the needle shield to expose the needle, such caps further hinder manual removal of the needle shield by the user resulting in a two-step process to expose the needle.

Therefore, a needle shield remover is desired that allows the cap and needle shield to be removed in a single step while reducing or eliminating inadvertent needle sticks.

BRIEF SUMMARY OF THE INVENTION

In one embodiment there is an apparatus for removing a needle shield from a syringe. The apparatus may be a remover including a proximal-to-distal axis, a body, and an arm which may be deflectable. The remover may be coupled to a syringe having a removable needle shield and the remover may be configured to receive the removable needle shield. The arm may include a distal end coupled to the body and a proximate end axially spaced from an end of the body. The deflectable arm may be configured to engage and apply a force to the needle shield when the remover is separated from the syringe, to thereby remove the needle shield from the syringe. The body may include an opening and the arm may be positioned within the opening.

In a further embodiment, there may be a cap detachably coupled to the injector and attached to the remover. A boss may extend from the cap and an aperture in the body may be configured to receive the boss to secure the remover to the cap. The remover may rotate relative to the needle shield while engaged with the needle shield. In a further embodiment, the remover may include a second deflectable arm, and the arms may be moveable between a first configuration wherein the arms are flexed radially outward and a second configuration wherein the arms are aligned with the body. The arms may be in the first configuration when the arms are adjacent the syringe. The arms may be in the second configuration when the arms are adjacent a proximal end of the needle shield.

A flange may extend distally from the arm and the flange may engage and apply a force to the proximal end of the needle shield when the cap is detached from the syringe. The proximal end of the deflectable arm may be proximal to a proximal end of the cap. The remover may include a central channel and the cap may include a projection extending proximally from a distal end of the cap and into the central channel when the remover is coupled to the cap.

In another embodiment there is an apparatus for removing a needle shield from a syringe. The apparatus may include a cap detachably coupled to a syringe having a removable needle shield, the cap may have a distal end and a projection extending proximally from the distal end. The apparatus may include a remover having a channel configured to engage the projection to secure the remover to the cap. The remover may be configured to receive the needle shield and apply a force to a proximal end of the needle shield when a force is applied to the cap to thereby remove the needle shield from the syringe. A boss may extend from the projection and an aperture in the remover may be configured to receive the boss to secure the remover to the cap. A proximal end of the remover may be proximal to a proximal end of the cap. The remover may include a body and an arm which engages the proximal end of the needle shield, and a proximal end of the arm may be distal to a proximal end of the body. The body may include an opening and the arm may be positioned in the opening. The arm and body may monolithically form the remover.

A flange may be coupled to the remover and extending distally therefrom. The flange may be configured to engage and apply a force to a proximal end of the needle shield when a force is applied to the cap. A diameter of the projection may be greater than or equal to a diameter of the needle shield. The body may include a circumferential halo proximal to the opening. The arm may be deflectable from a first position to a second position as the needle shield is positioned within the remover. In a further embodiment, the remover includes at least one additional opening in the body, and the openings in the body may be separated by struts. A halo may connect a proximal end of the struts.

BRIEF DESCRIPTION OF THE SEVERAL VIEWS OF THE DRAWINGS

The foregoing summary, as well as the following detailed description of embodiments of the needle-shield remover, will be better understood when read in conjunction with the appended drawings of an exemplary embodiment. It should be understood, however, that the invention is not limited to the precise arrangements and instrumentalities shown.

In the drawings.

DETAILED DESCRIPTION OF THE INVENTION

Figure 1:
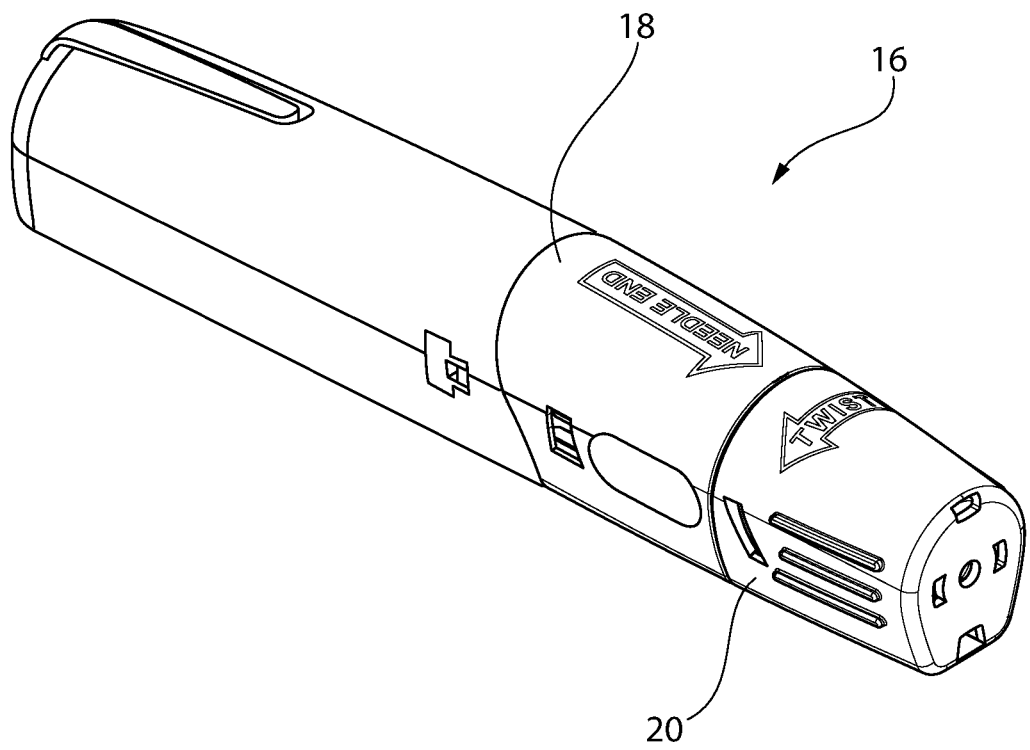
FIG. 1 is a side perspective view of an injector which includes a cap in accordance with an exemplary embodiment of the present invention.

Referring to the drawings in detail, wherein like reference numerals indicate like elements throughout, there is shown in FIGS. 1-13 an injector, generally designated 16, in accordance with an exemplary embodiment of the present invention. As shown in FIG. 1, the injector 16 may include an outer housing 18 which houses a syringe 17 (see FIG. 12). The injector 16 may include a cap 20 coupled to the outer housing 18.

Figure 2:
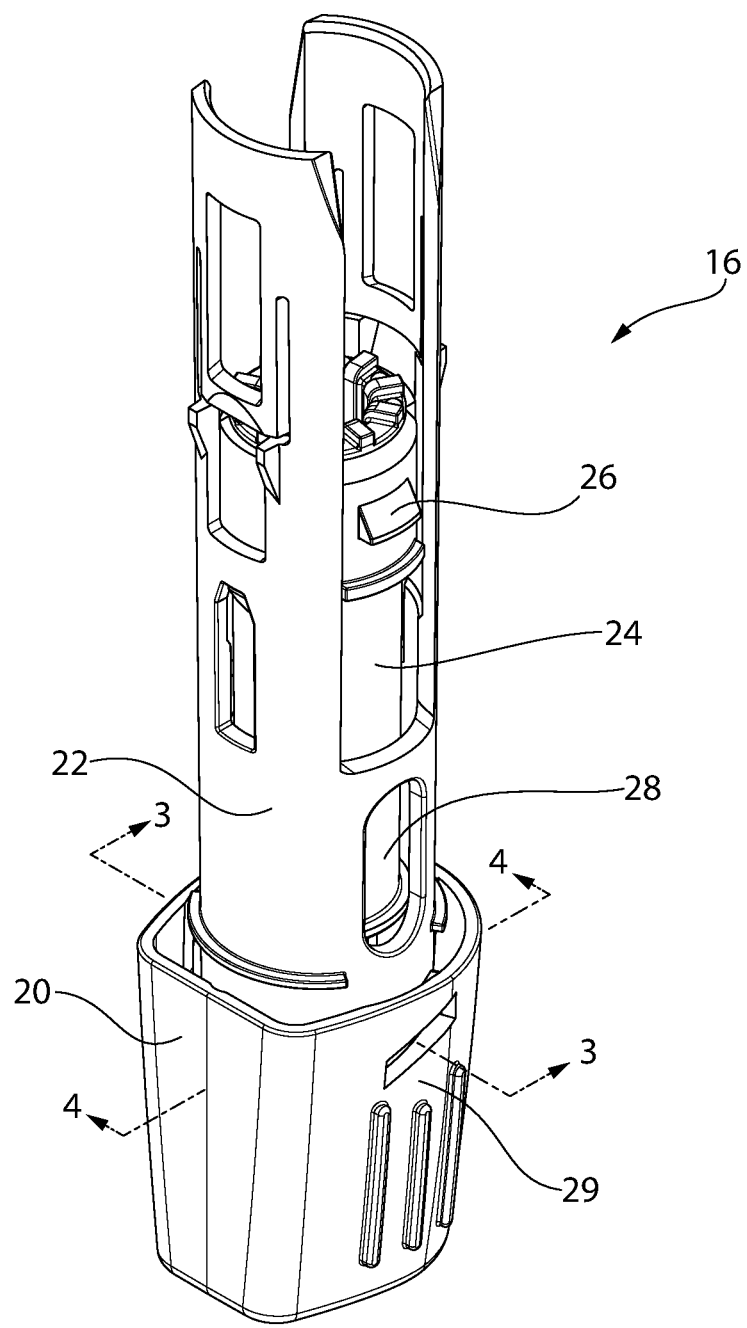
FIG. 2 is a side perspective view of the injector of FIG. 1 with the outer housing removed.
Figure 12:
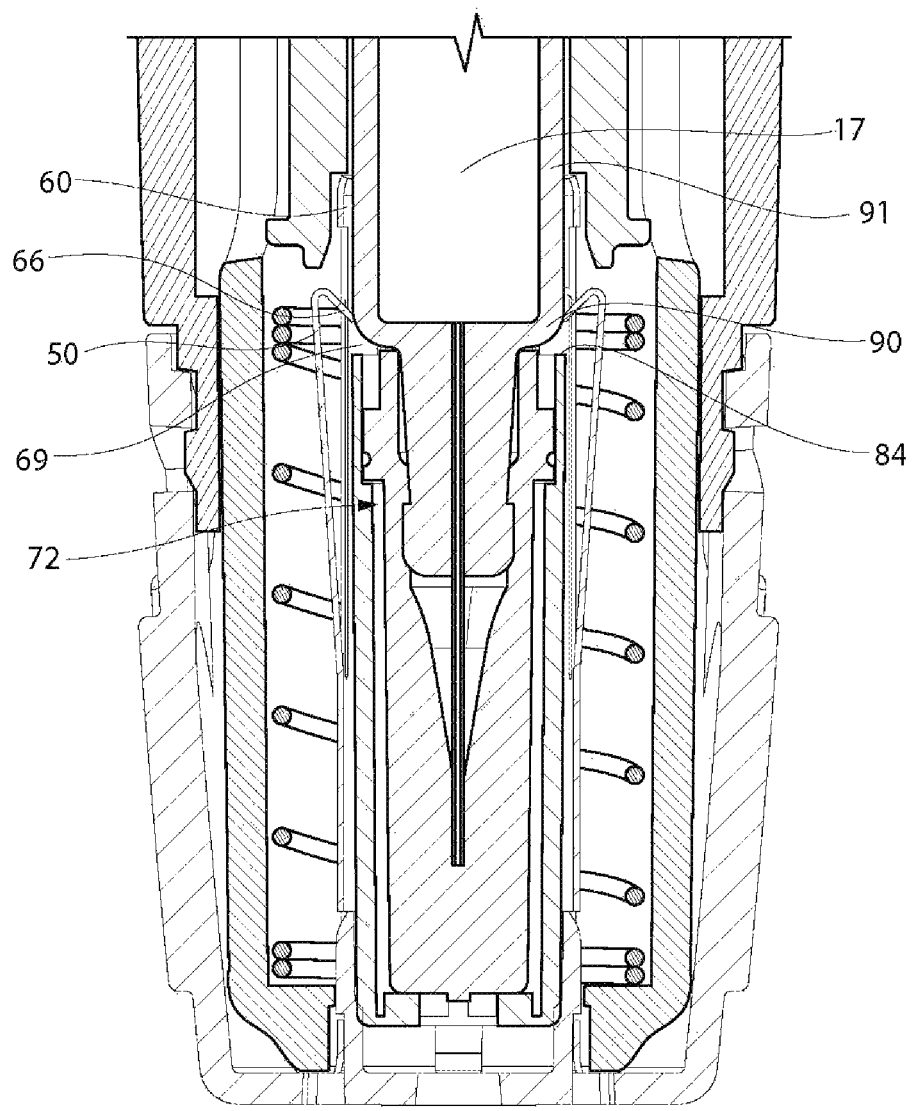
FIG. 12 is a side sectional view of the injector of FIG. 1 shown taken about a plane, the location and direction being indicated by line 4-4 in FIG. 2 and with the arms of the remover in a flexed configuration.

Referring to FIGS. 2 and 12, the injector 16 may receive a syringe 17 (FIG. 12) to inject medicament into a patient or user. In one embodiment, the syringe 17 is prefilled with a medicament. The tip of the needle may be covered by a needle shield 72 (FIG. 12) before the syringe is inserted into the injector 16 during assembly. The injector 16 may include a guard 22 and a sleeve 24. The guard 22 may be positioned in the outer housing 18 and the sleeve 24 may be positioned in the guard 22. The sleeve 24 may have a passageway extending therethrough to receive at least a portion of the syringe 17. The sleeve 24 may include a projection 26 and the guard 22 may have a channel 28. The syringe 17 and sleeve 24 may be within the guard 22 when the injector 16 is in a storage position. The guard 22 may be retractable relative to the outer housing 18 and sleeve 24 such that the needle of the syringe 17 is exposed (not shown) when the injector 16 is an injection position. A ram (not shown) may move a piston (not shown) in the syringe 17 to deliver medicament from the syringe 17 to the patient. One example of such a ram is described in U.S. Patent Application Publication No. 2013/0331788, the disclosure of which is hereby incorporated by reference herein.

Figure 3:
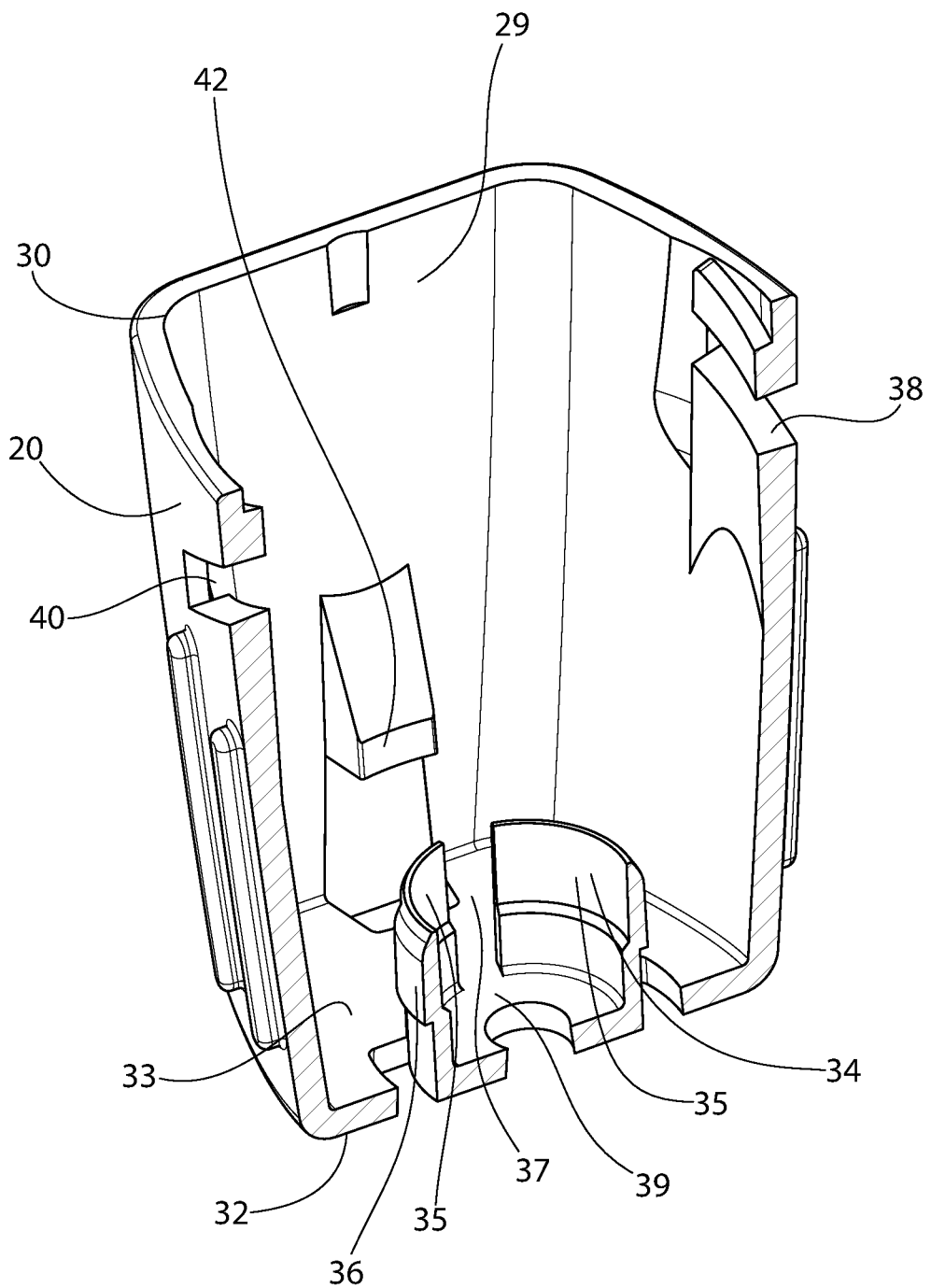
FIG. 3 is a perspective sectional view of the cap of FIG. 1 shown taken about a plane, the location and direction being indicated by line 3-3 in FIG. 2.

Referring to FIG. 3, there is shown a sectional view of the cap 20 along a plane, the location and direction being indicated by line 3-3 of FIG. 2. The cap 20 may include one or more sidewalls 29 which generally form a receptacle to receive at least a portion of the guard 22. The cap 20 may include a proximal end 30 and a distal end 32. The distal end 32 may include a distal surface 33 at least partially sealing the distal end 32 of the cap 20. A projection 34 may extend from the distal surface 33 toward the proximal end 30. In one embodiment, the projection 34 is circular and smaller in diameter than a diameter of a needle shield associated with the syringe 17. In other embodiments, the projection 34 is circular and has the same or larger diameter than the needle shield 72 (see FIG. 12). The projection 34 is not limited to being circular but may be any desired shape such as square or oval. The projection 34 may be a singular element or may include one or more sections 35 that are separated by a relief 37. A relief 37 may allow the sections 35 to move relative to each other from a relaxed configuration to a contracted configuration. A boss 36 may extend from the projection 34. The projection 34 may include a bore 39 defined by the sections 35. Threads 38 may be formed on the cap 20 which engage corresponding threads on the outer housing 18 and secure the cap 20 to the outer housing 18. A hole 40 may be formed between the thread 38 to allow a user to visually confirm that the thread on the outer housing 18 is properly engaged with the thread 38 on the cap 20. The cap 20 may include a protuberance 42 which may couple to the guard 22 to further secure the cap 20 to the outer housing 18.

Figure 4:
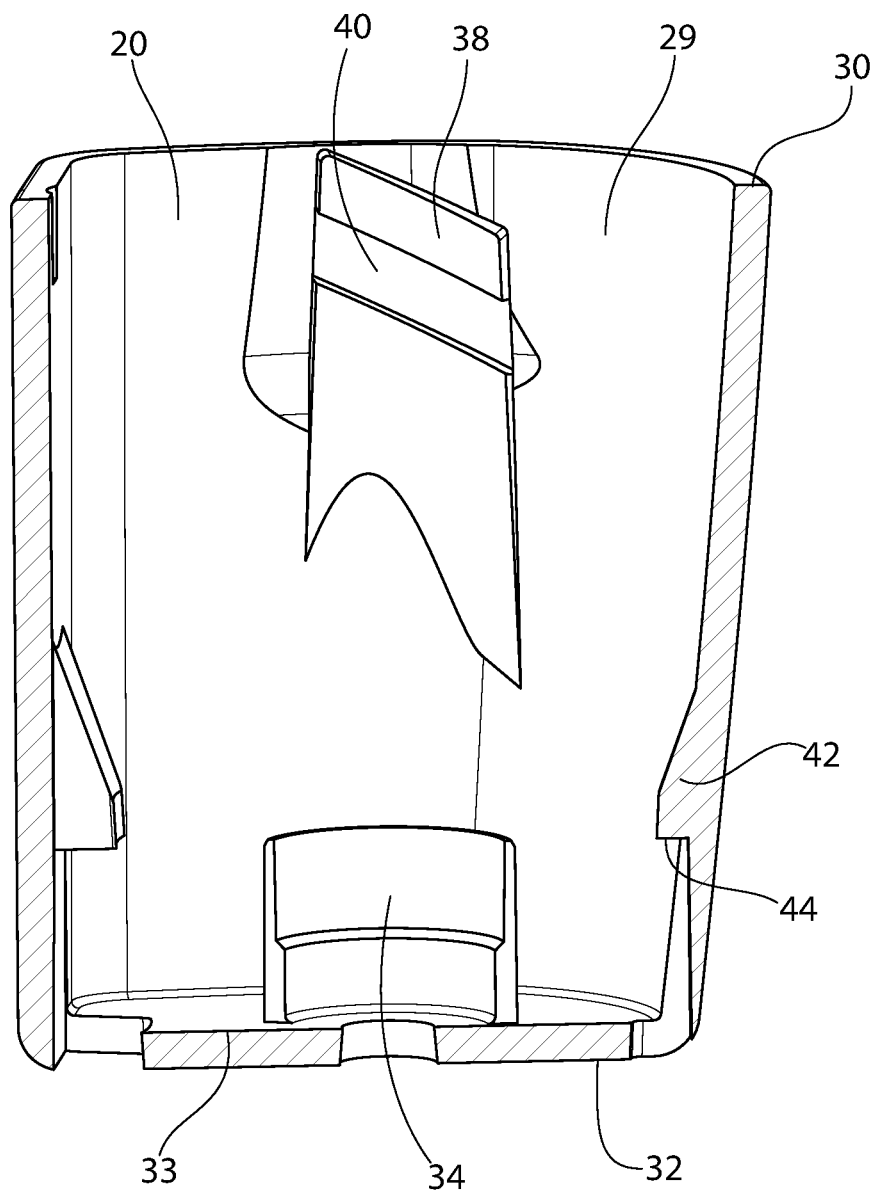
FIG. 4 is a side sectional view of the cap of FIG. 1 shown taken about a plane, the location and direction being indicated by line 4-4 in FIG. 2.

Referring to FIG. 4, there is shown a sectional view of the cap 20 along a plane, the location and direction being indicated by line 4-4 of FIG. 2. The protuberance 42 may include a shoulder 44 or generally flat surface which engages a similar, but oppositely facing protuberance on the guard 22. The cap 20 may be formed from any material (e.g. metal, plastic). In one embodiment, the interaction between the protuberance 42 of the cap 20 and the protuberance on the guard 22 prevents the guard from moving in the proximal direction spontaneously such as when the injector is dropped, accidentally contacted, etc.

Figure 5:
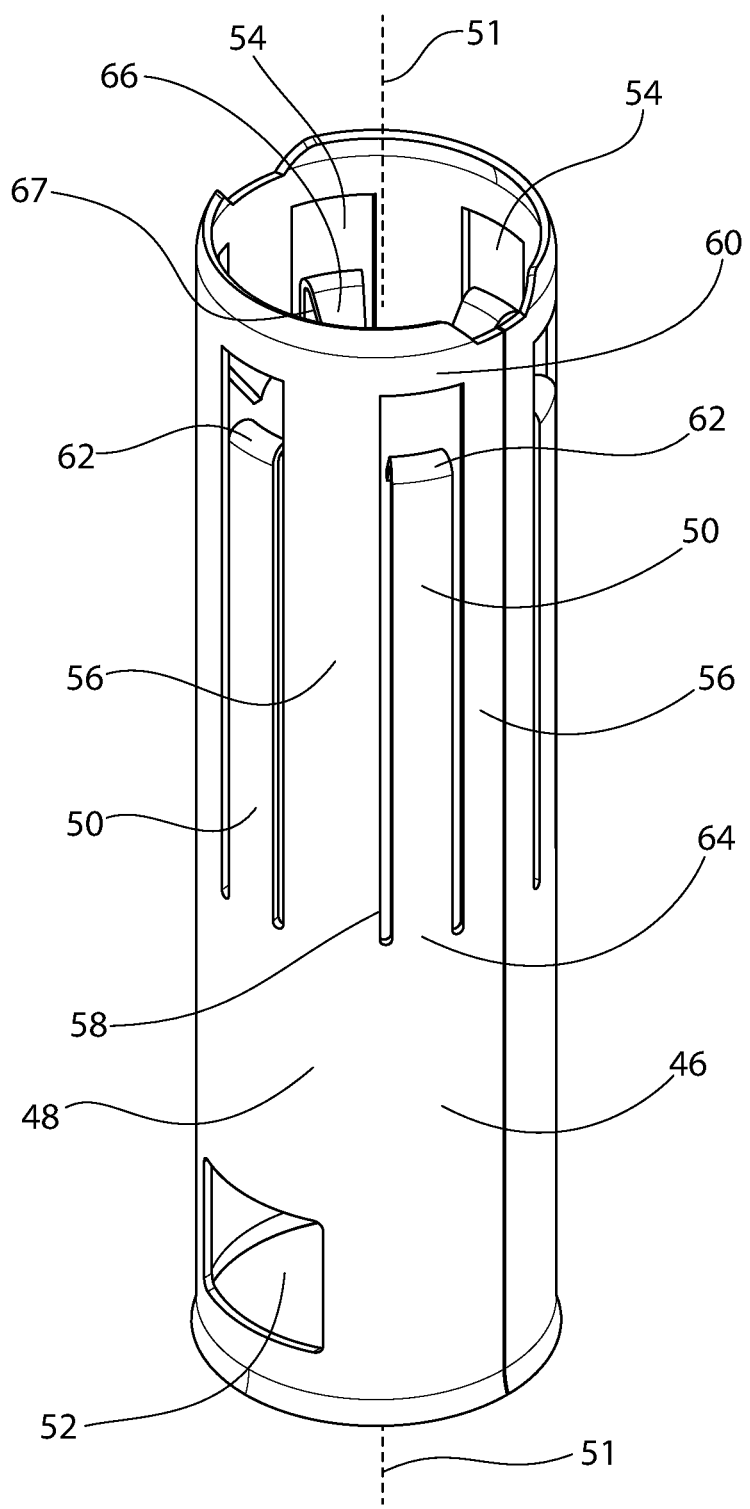
FIG. 5 is a top perspective view of a remover in accordance with an exemplary embodiment of the present invention.

Referring to FIG. 5, there is shown a top perspective view of a remover 46 which extends along a proximal-to-distal axis 51. The remover 46 may include a body 48 and one or more arms 50. In one embodiment, the body 48 and arms 50 are monolithic with one another. In another embodiment, the arms 50 and body 48 are formed separately and coupled together via adhesive, welding, hinges, screws, etc. The arms 50 may be cantilevered to the body 48 and deflectable from a relaxed configuration (shown in FIG. 5) wherein the arms 50 are separated by a first distance, to an expanded configuration (shown in FIG. 12) wherein the arms are separated by a second distance different than the first distance. The arms 50 may be generally parallel with the body 48 in the relaxed configuration and extend radially outwardly from the body 48 in the expanded configuration. In another embodiment, the arms 50 extend radially inwardly from the body 48 in the relaxed configuration. In one embodiment, the remover 46 includes between 1 and 10 arms. In one embodiment, the remover includes between 3 and 8 arms. In one embodiment, the remover 46 includes between 5 and 7 arms. In one embodiment, the remover 46 includes 6 arms. In one embodiment, the arm 50 has a length along the axis 51 of about 0.2 inches to about 1.0 inches, about 0.3 inches to about 0.9 inches, about 0.4 inches to about 0.8 inches, about 0.5 inches to about 0.7 inches, about 0.2 inches, about 0.3 inches, about 0.4 inches, about 0.5 inches, about 0.6 inches, about 0.7 inches, about 0.8 inches, about 0.9 inches, or about 1.0 inches. In one embodiment, the length of the arm 50 is selected to reduce or eliminate stress and/or fatigue in the arm as the arm flexes as explained in greater detail below. In one embodiment, the arms have a width as measured along the perimeter of the remover 46 of about 0.01 inches to about 0.05 inches, about 0.02 inches, about 0.03 inches, or about 0.04 inches. In one embodiment, the arms 50 have a thickness of about 0.005 inches, about 0.01 inches, about 0.015 inches, about 0.02 inches, about 0.025 inches, about 0.03 inches, about 0.04 inches, or about 0.05 inches.

In one embodiment, an aperture 52 is formed in the body 48 to receive the boss 36 and secure the remover 46 to the cap 20. The aperture 52 may have the same general shape as the boss 36 or may be larger than the boss 36 to allow some movement of the remover 46 with respect to the projection 34 when the boss 36 is within the aperture 52. In one embodiment, the aperture 52 is elongated such that the boss 36 can move relative to the aperture 52 as the cap 20 is rotated while the remover 46 is rotationally fixed relative to the syringe 17. The remover 46 may include any number of apertures 52 such that the alignment of the remover 46 with respect to the projection 34 may be changed as desired. In another embodiment, the remover 46 includes a recess, hook, deformable section, etc. to receive the boss 36. In other words, the remover 46 may include an engaging element which allows it to operatively associate with the cap 20 through a feature present in the projection 42 such as a boss 36 that is part of the projection 42 which may be received by the aperture 52 in the remover 46. In one embodiment, the boss 36 is formed on the remover 46 and the aperture is formed on the projection 34. In another embodiment, the remover 46 includes at least one boss and at least one aperture which cooperate with at least one boss and at least one aperture on the projection 34 to secure the remover 46 to the cap 20. In another embodiment, the engaging elements on the cap and remover provide a temporary connection that allow cap and remover to be simultaneously coupled to the injector and needle shield, but the cap is decoupled from the injector and remover prior to using the remover to remove the needle shield. In another embodiment (not shown), the remover 46 is connected to a cap which is not coupled to an injector. In such an embodiment, the cap may be a handle, a bulb with two handles, a hook, or any other feature which allows a user to grasp the remover to remove a needle shield by directly coupling the remover to the syringe and needle shield.

With continued reference to FIG. 5, the body 48 may include openings 54 spaced about the remover 46. In one embodiment, the body 48 includes between 1 and 10 openings. In another embodiment, the body 48 includes between 3 and 9 openings. In another embodiment, the body 48 includes between 4 and 8 openings. In another embodiment, the body 48 includes between 5 and 7 openings. In another embodiment, the body includes 6 openings. In some embodiments, an arm 50 is within each opening 54. In other embodiments, some openings 54 do not have an arm 50 within them. In one embodiment, the openings 54 are equally spaced about the body 48. In other embodiments, the openings 54 are not equally spaced about the body 48. In one embodiment, the center of the openings 54 are circumferentially spaced about 60° from each other. In another embodiment, the centers of the openings 54 are circumferentially spaced between about 50° and about 70° from each other. In another embodiment, the centers of the openings 54 are circumferentially spaced between about 40° and about 80° from each other. In another embodiment, the centers of the openings 54 are circumferentially spaced between about 30° and about 90° from each other. In another embodiment, the centers of the openings 54 are circumferentially spaced between about 100° and about 150° from each other. The openings 54 may be separated by struts 56. A space 58 may separate a side of the strut 56 from a side of the arm 50. The struts 56 may prevent misalignment of the arms 50 (e.g. by twisting, bending) as the needle shield is positioned within the remover 46 as explained in greater detail below.

A halo 60 may extend circumferentially around the remover 46 and connect the struts 56 to each other. A halo 60 which extends around the perimeter of the remover 46 may provide hoop strength or rigidity to the remover 46 as the arms 50 flex. The halo 60 may have an inner diameter similar to or the same as the inner diameter of the body 48. In another embodiment, the inner diameter of the halo 60 is larger than the inner diameter of the body 48. The halo 60 may be flared out compared to an adjacent portion of the remover 46. In one embodiment, the inner diameter of the halo 60 may be selected based on the outer diameter of the syringe which the remover 46 will be coupled to. The remover 46 may be used with a syringe barrel having any diameter which fits within the halo 60. The remover 46 may have a halo 60 and body 48 with an inner diameter sufficiently large to accommodate the outer diameter of the syringe barrel 91. In one embodiment, the halo may have an inner diameter of about 0.1 inches, about 0.2 inches, about 0.3 inches, about 0.4 inches, about 0.5 inches, about 0.6 inches, or about 0.7 inches. The halo 60 may be positioned proximate of a proximal end 62 of the arms 50 such that a proximal end 62 of the arms is distal, or axially spaced from, a proximate end of the body 48. In one embodiment, the halo 60 is a continuous element which extends around the perimeter of the remover 46. In other embodiment, the halo 60 is formed of at least two discrete elements each extending around a portion of the remover 46. A distal end 64 of the arms 50 may be connected to the body 48 and rest of the arms may be otherwise surrounded by the body 48 and the halo 60. The halo 60 may be spaced from the proximate end 62 of the arms 50. The arms 50 may include a flange 66 on the proximate end 62. The flanges 66 may engage and apply a force to the needle shield when the cap 20 is detached from the syringe to remove the needle shield from the syringe. A nook 67 may be formed between the flange 66 and the arm 50. The flange 66 may extend away from the arm 50 at an angle of about 10°, about 20°, about 30°, about 40°, about 50°, about 60°, or about 70°. The nook 67 may engage the needle shield as the cap 20 is separated from the injector 16. In another embodiment, the flanges 66 engage and apply a force to the needle shield 72 when the remover 46 is moved distally from the syringe 17 and such continued distal motion of the remover causes the removal of the needle shield from the syringe. In other embodiments of the remover 46, the flanges 66 include a nook 67 which engages the needle shield upon distal movement of the remover 46 on the syringe.

Figure 6:
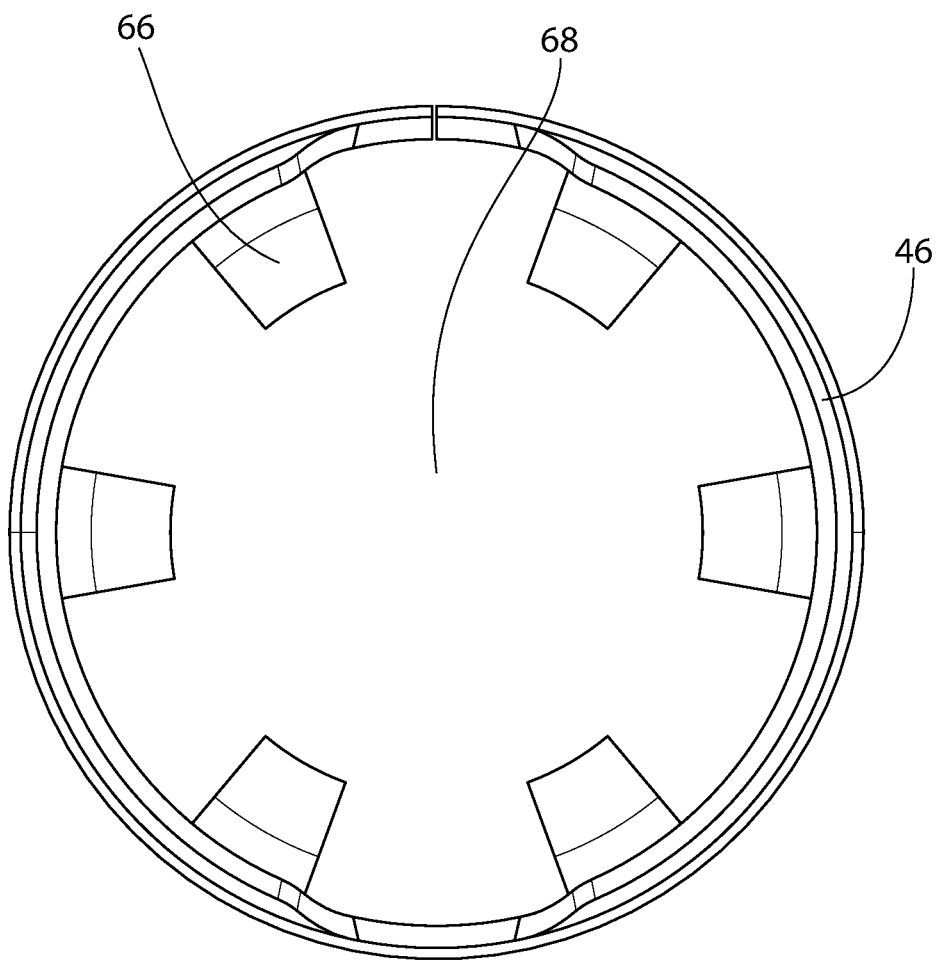
FIG. 6 is a top view of the remover of FIG. 5.

Referring to FIG. 6, the remover 46 may have a central channel 68 to receive the needle shield. In some embodiments, the central channel 68 has an internal diameter equal to an outer diameter of the needle shield. In other embodiments, the central channel 68 has an internal diameter slightly larger than an outer diameter of the needle shield. In one embodiment, the remover forms a complete circle when viewed from the top. In other embodiments, the remover 46 forms an open ended arc. In still other embodiments, the remover 46 forms a square, ellipse, triangle, etc. In other words, the remover 46 may take any shape provided that the needle shield can be positioned within the central channel 68. The flanges 66 may extend into the central channel 68 when the arms 50 are in the relaxed configuration. In one embodiment, a portion of the arms 50 extend into the central channel 68. In one embodiment, the flanges 66 extend into the central channel 68 and contact one another. In one embodiment, an end of each of the flanges 66 lie on an imaginary circle having a diameter of about 0.1 inches, about 0.2 inches, about 0.3 inches, or about 0.4 inches. The needle shield 72 may contact the flanges 66 as the needle shield is inserted into the central channel 68 and the arms 50 may engage the needle shield 72. The needle shield 72 may push the flanges 66 radially outwardly from the relaxed or second configuration and into the expanded or first configuration as the needle shield 72 is inserted into the central channel 68. In one embodiment, the arms 50 flex as the needle shield 72 is inserted into the central channel 68. In another embodiment, the arms 50 remain stationary and only the flanges 66 flex as the needle shield 72 is inserted into the central channel. In yet another embodiment, both the arms 50 and the flanges 66 flex as the needle shield 72 is inserted into the central channel 68. The arms 50 may return to the relaxed configuration when the flanges 66 are proximate a proximal end of the needle shield 72. The flanges 66 may be angled distally to slide over the needle-shield and the syringe during assembly and grasp the needle-shield during removal as discussed in further detail below.

Figure 7:
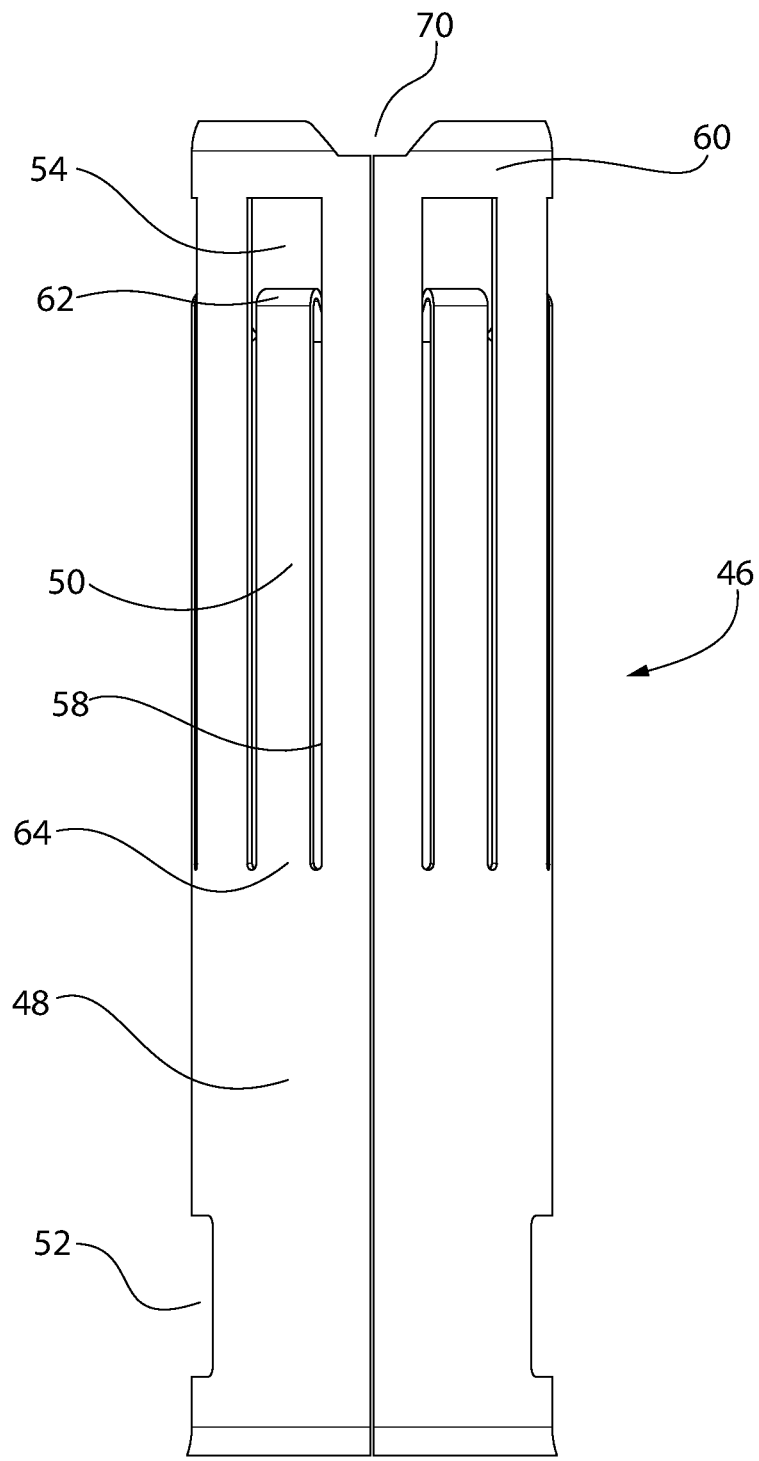
FIG. 7 is a side view of the remover of FIG. 5.

Referring to FIG. 7, the remover 46 may have a recess 70 formed in the proximal end of the halo 60. The recess 70 may be a sunk recess for manufacturing. In those embodiments where the remover 46 is a monolithic element, the remover 46 may be formed from a planar material (e.g. sheet metal). The material may be cut (e.g. laser cut) to create the spaces 58 separating the arms 50 from the body 48. A cut may be made at the proximal end of the arms 50 to separate the arm 50 from the halo 60. The proximal end of the arm 50 may be bent to create the flange 66. The body 48 may be rolled into a cylinder (or any other desired shape) and coupled via welding, adhesive, etc. The remover 46 may be detachably coupled to the cap 20. A user may couple the remover 46 to the cap 20 by positioning the remover about the projection 34 (FIG. 3). The sections 35 of the projection 34 (FIG. 3) may flex inwardly as the remover 46 is secured to the cap 20 and return to their relaxed position when the boss 36 is within the aperture 52.

Figure 8:
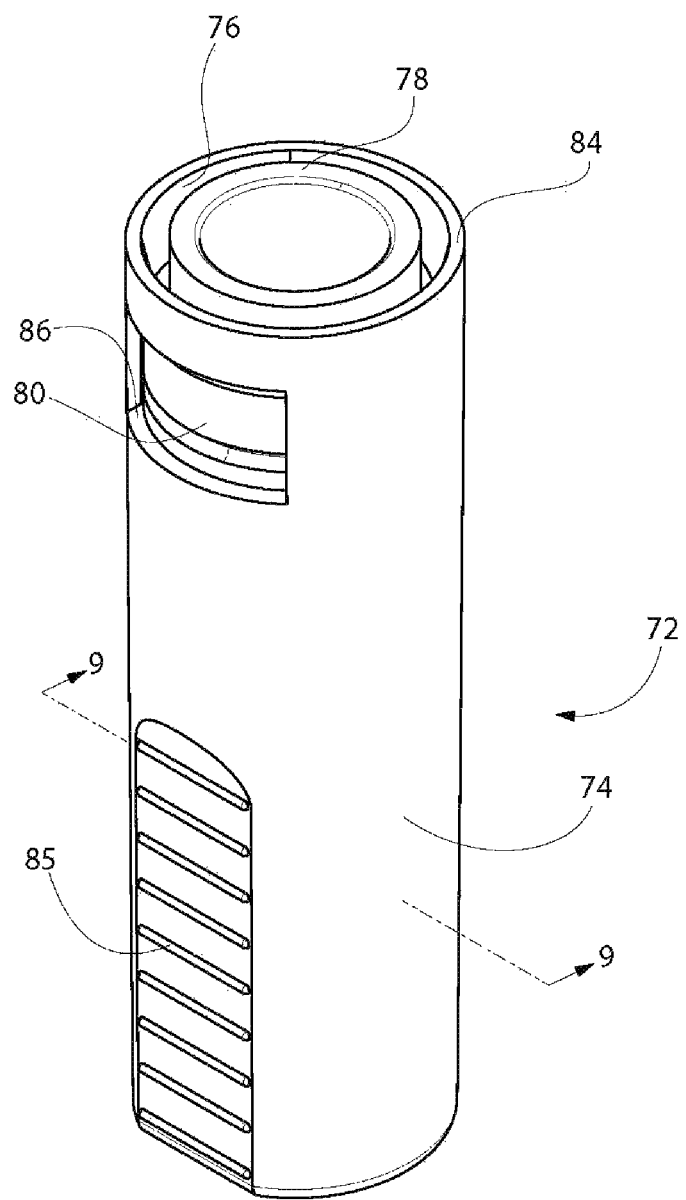
FIG. 8 is a top perspective view of an outer member of a needle shield.

Referring to FIG. 8, a needle shield 72 may include an outer member 74. The outer member 74 may comprise a rigid material to protect the needle from damage and prevent accidental sticks to a person handling the syringe. The outer member 74 may include a receptacle 76 to receive an inner member 78. An opening 80 may be formed in the outer member 74 to receive an extension 82 on the inner member 78. Ridges 85 may be formed on an outer surface of the outer member 74. The ridges 85 may provide a textured surface to improve a user's grip if they grasped the needle shield 72 to remove it from the syringe. However, the cap 20 may automatically remove the needle shield 72 from the syringe when the cap 20 is detached from the injector 16 and eliminate the need for a user to manually grasp the needle shield 72. In one embodiment, the remover 46 is independent from the cap 20 such that the cap 20 is removed from the injector 16 prior to coupling the remover 46 to the needle shield 72. In a further embodiment, the independent remover 46 is nested within the cap 20 such that the remover 46 is coupled to the needle shield 72 when the cap 20 is initially coupled to the injector 16. The cap may then be detached from the injector 16 while the remover 46 remains coupled to the needle shield 72 and the user can remove the needle shield with the remover 46 when desired. A rim 84 may be formed on a proximal end of the outer member 74. The rim 84 may provide a surface engageable by the flange 66 as explained below. A lip 86 may be formed within the receptacle 76 adjacent the opening 80. The lip 86 may assist in maintaining the position of the inner member 78 when the syringe is within the needle shield 72. Alternatively, the rim 84 may provide a surface engageable by the nook 67 or the flange 66.

Figure 9:
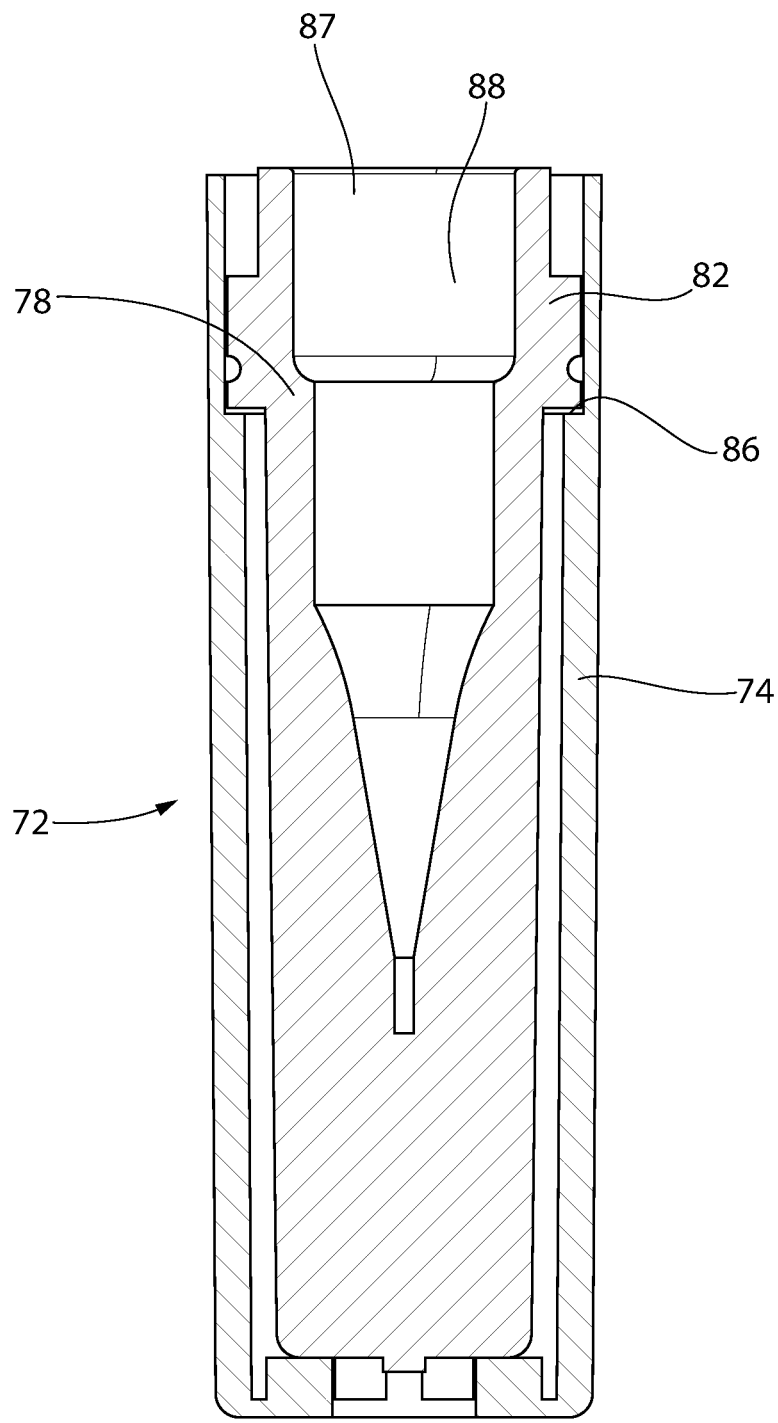
FIG. 9 is a side sectional view of the outer member of FIG. 8 shown taken about a plane, the location and direction being indicated by line 9-9 in FIG. 8 and with an inner member of a needle shield positioned therein.

Referring to FIG. 9, a sectional view along a plane, the location and direction being indicated by line 9-9 of the needle shield 72 is shown. The inner member 78 may be positioned within the outer member 74 such that a lower surface of the extension 82 is adjacent the lip 86. The inner member 78 includes a cutout 88 shaped to receive the syringe. The cutout 88 may be adapted to receive any size or shape syringe desired. The inner member 78 may comprise a flexible material (e.g. rubber, silicone) to prevent the needle from being damaged by the outer member 74.

Figure 10:
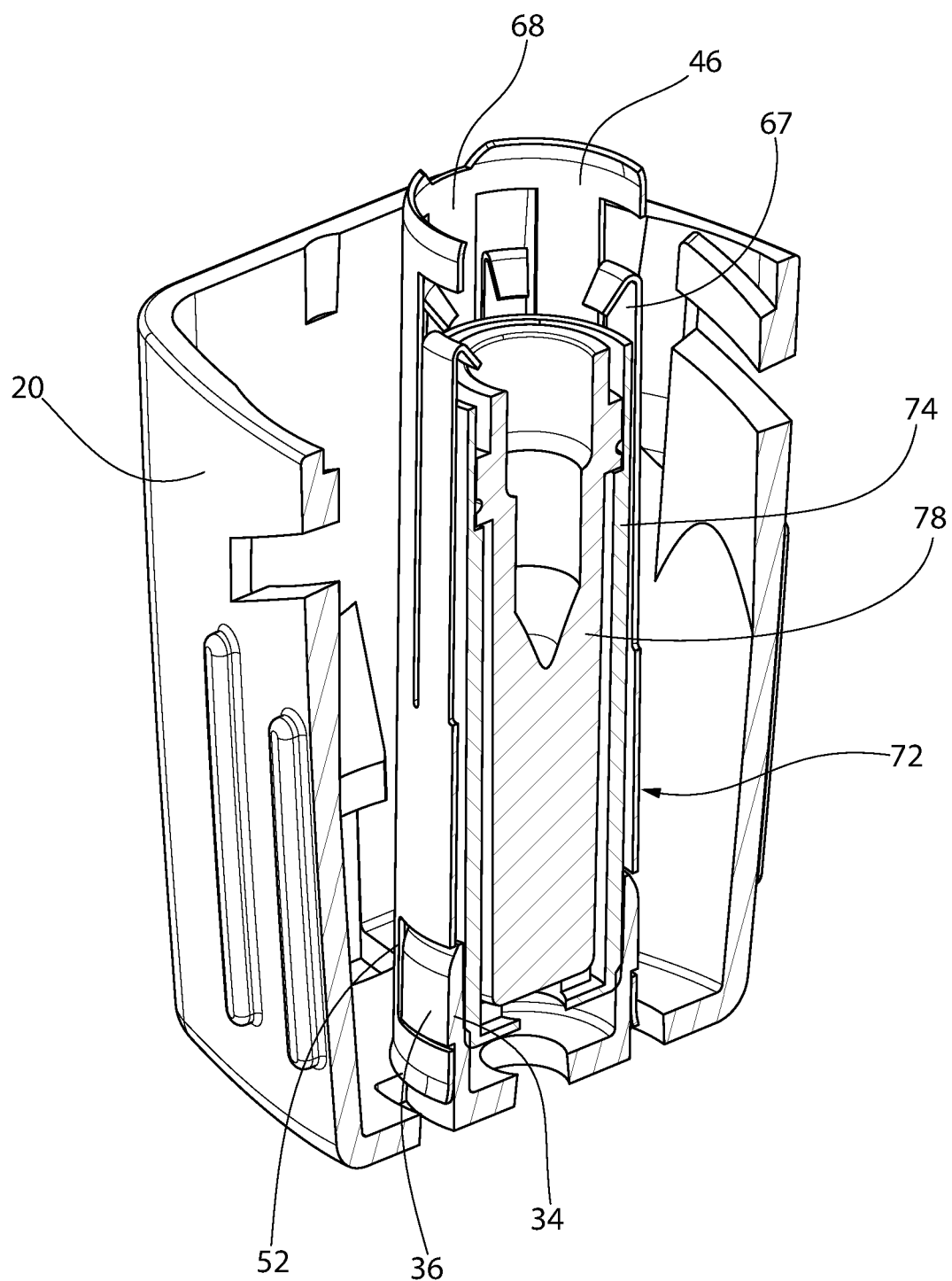
FIG. 10 is a top perspective sectional of the injector of FIG. 1 shown taken about a plane, the location and direction being indicated by line 4-4 in FIG. 2 and with the outer housing and guide removed.

Referring to FIG. 10, a sectional view of the cap 20 along a plane, the location and direction being indicated by line 4-4 of FIG. 2 is shown. In one embodiment, the remover 46 may be attached to the cap 20 such that the projection 34 is within the central channel 68. The remover 46 and projection 34 may be aligned such that the boss 36 is within the aperture 52. In another embodiment, the remover 46 may be positioned within the bore 39 (FIG. 3) and the boss 36 may extend inwardly into the aperture 52. The boss 36 within the aperture 52 may prevent relative rotation between the cap 20 and the remover 46. In one embodiment, the distal end of the remover 46 is adjacent the distal end of the cap 20 when the boss 36 is within the aperture 52. In another embodiment, the distal end of the remover 46 is spaced from the distal end of the cap 20 when the boss 36 is within the aperture 52. The proximal end of the arm 50 may be proximate the proximal end of the needle shield 72 when the needle shield 72 is inserted into the central channel 68 of the remover 46. The needle shield 72 may be rotatable relative to the remover and cap 20 when the needle shield 72 is within the central channel 68. For example, the cap 20 may be rotated relative to the injector 16 to disengage the thread 38 of the cap 20 from threads on the injector 16 while the needle shield 72 is within the central channel 68. It is believed that allowing relative rotation between the remover 46 and needle shield 72 prevents misalignment or damage to the arms 50 or flanges 66 as the cap 20 is removed.

Figure 11:
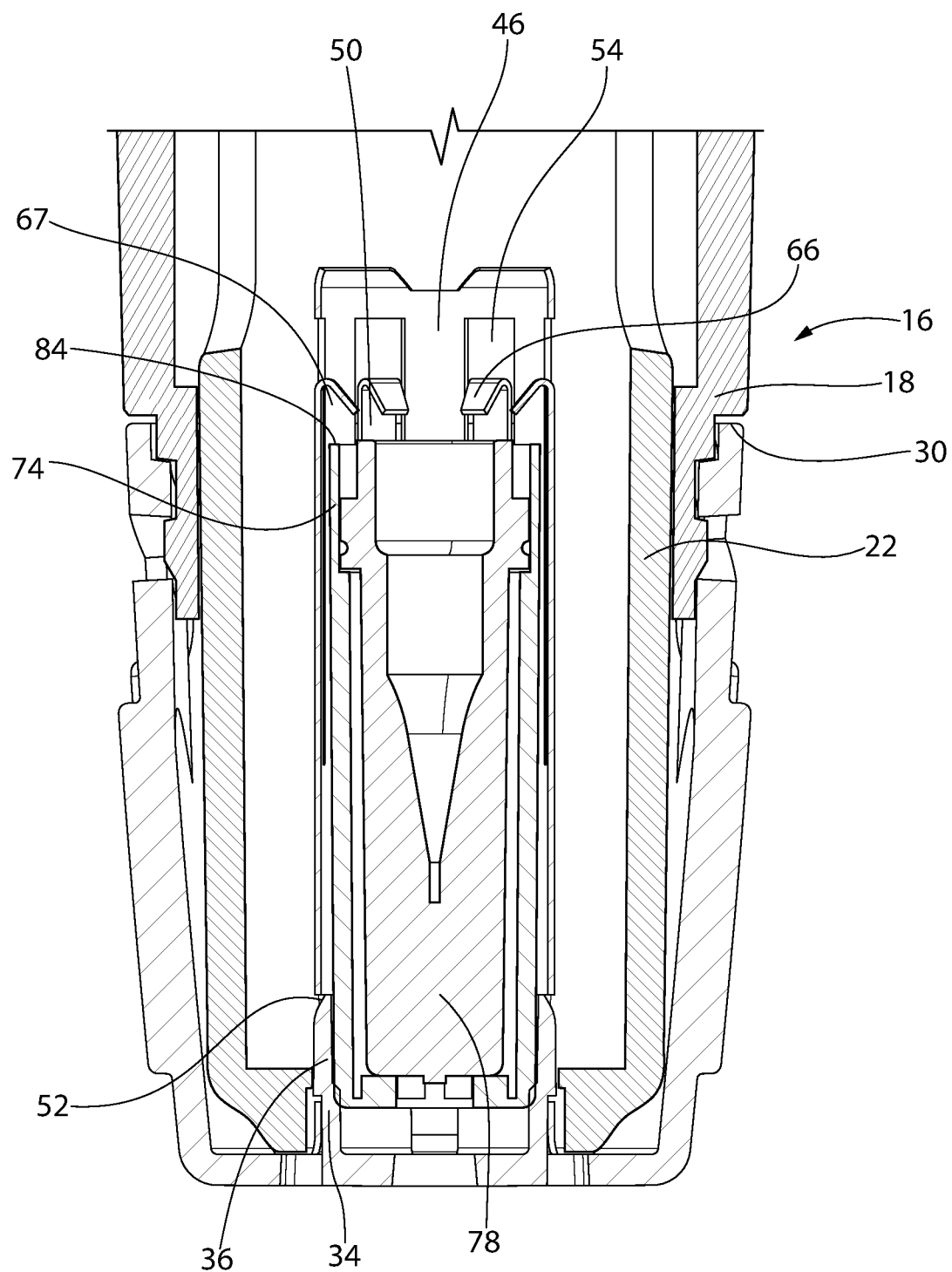
FIG. 11 is a side sectional view of the injector of FIG. 1 shown taken about a plane, the location and direction being indicated by line 4-4 in FIG. 2 and with the guide removed and the arms of the remover in a relaxed configuration.

Referring to FIG. 11, the proximal end of the remover 46 may be proximal to a proximal end 30 of the cap 20 when the remover 46 is coupled to the cap 20. The remover 46 may be at least partially positioned within the outer housing 18 and the guard 22 when the cap 20 is coupled to the injector 16.

Referring to FIG. 12, the arms 50 may be in the expanded configuration when the cap 20 is coupled to the injector and the flanges 66 engage a location on or proximal to the shoulder 90 on the syringe 17. In one embodiment, the arms 50 are in the relaxed configuration when the cap 20 is not coupled to the injector and the arms 50 radially flex an initial amount when the needle shield 72 is first inserted into the remover 46 and the flanges 66 contact the needle shield 72. The arms 50 may radially flex an additional amount when the flanges 66 engage a location on or proximal to the shoulder 90 of the syringe 17. Having the flanges 66 rest on the barrel 91 of the syringe 17 rather than attempting to position them in the space 69 between the needle shield 72 and the syringe 17 may allow for component and assembly tolerances that could make it difficult to precisely position the flanges 66. The halo 60 may be adjacent to or in contact with the syringe barrel 91 and the flanges 66 in contact with the syringe 17 such that the arms 50 are radially flexed when the needle shield 72 is fully within the remover 46. In one embodiment, the arms 50 are not required to be in the relaxed configuration to engage and remove the needle shield 72. For example, the arms 50 could be flexed when they engage the needle shield 72.

Figure 13:
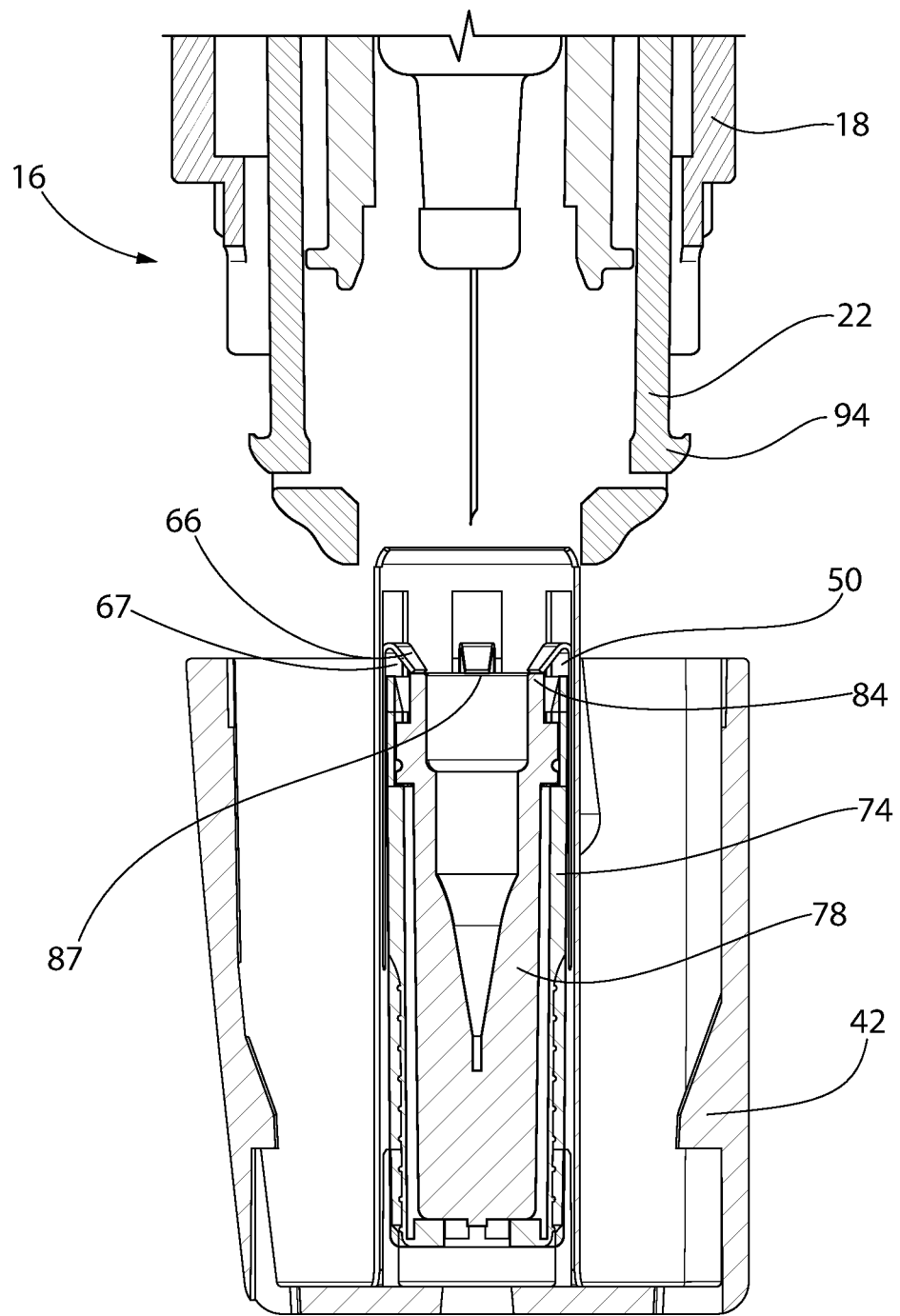
FIG. 13 is side sectional view of the injector of FIG. 1 shown taken about a plane, the location and direction being indicated by line 3-3 in FIG. 2 and with the arms of the remover engaged on the needle shield and the needle shield removed from the needle.

Referring to FIG. 13, the user may rotate the cap 20 to disengage the thread 38 from the thread on the outer housing 18. Rotating the cap may also disengage the protuberance 42 of the cap 20 from the protuberance 94 of the guard 22. In one embodiment, the flanges 66 on the arms 50 may slide along the body of the syringe 17 as the cap 20 is twisted relative to the syringe. In other words, the cap 20 and arms 50 can rotate relative to, and independently from, the syringe 17 when the cap 20 is engaged with the injector 16. The user may move the cap 20 distally relative to the injector 16 to separate the cap 20 from the injector 16. The arms 50 move radially inwardly as the as the cap 20 moves distally relative to the injector 16 such that the flanges 66 slide into the space 69 (shown in FIG. 12) between the rim 84 of the outer member 74 and the syringe 17 to engage the rim 84. In another embodiment, the arms 50 move radially inwardly as the as the cap 20 moves distally relative to the injector 17 such that the flanges 66 slide into the space 69 (shown in FIG. 12) between the proximate edge 87 (shown in FIG. 9) of the inner member 78 and the syringe 17 to engage the proximate edge 87. In one embodiment, an end of the flange 66 engages the rim 84 of the outer member 74. In an alternate embodiment, an end of the flange 66 engages the proximate edge 87 of the inner member 78. In another embodiment, the flange 66 extends inwardly beyond the outer member 74 and the rim 84 is positioned within the nook 67 such that an inner surface of the flange 66 engages the rim 84. In an alternate embodiment, the flange 66 extends inwardly beyond the inner member 78 and its proximate edge 87 and is positioned within the nook 67 such that an inner surface of the flange 66 engages the proximate edge 87. In yet another embodiment, the flange 66 engages the ridges 85 on the side of the needle shield 72. The needle shield 72 is removed from the syringe 17 when the user continues to move the cap 20 away from the syringe 17. In one embodiment, the needle shield 72 may be removed from the remover 46 and the cap 20 may be re-used to remove additional needle shields 72. In another embodiment, the needle shield 72 remains in the remover 46 but the remover is removable from the cap 20. The user may attach an additional remover 46 to the cap 20 to remove an additional needle shield 72. In yet another embodiment, the shield 72 is fixed within the remover 46 and cap 20 and cannot be removed. The cap 20 may be re-secured to the injector 16 to prevent inadvertent sticks.

Although the remover 46 has been described in connection with the cap 20, syringe 17, and injector 16 described herein, the remover could also be adapted to be used with any cap and injector or syringe. For example, the remover could be used with the devices disclosed in U.S. Pat. Nos. 6,565,553; 7,341,575; 7,488,308; 7,503,907; 8,562,564; 8,696,618; 8,758,299; and U.S. Patent Publication No. 2016/008543; the disclosures of which are hereby incorporated by reference herein. Alternatively, the remover 46 can be described in connection with syringe 17 to affect the removal of needle shield 72.

Figure 14:
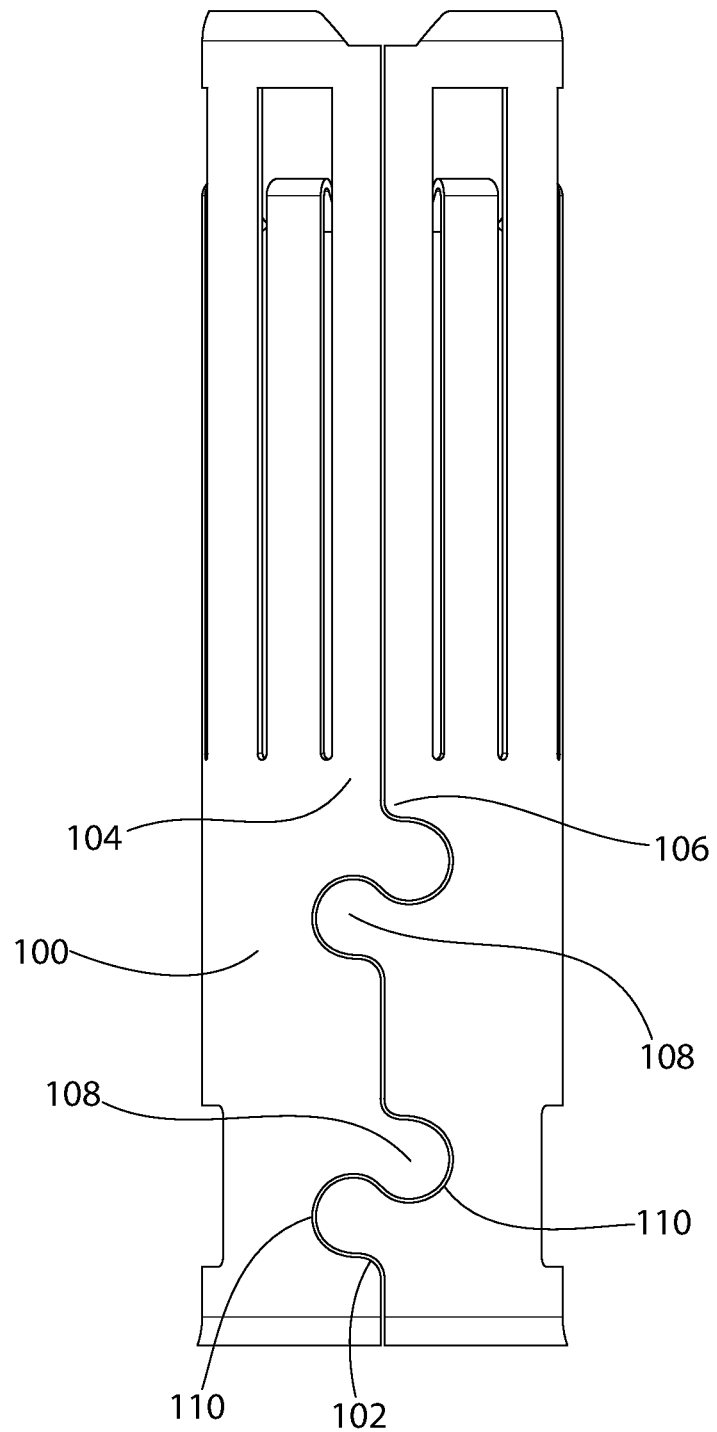
FIG. 14 is a side view of another exemplary embodiment of the present invention.

Referring to FIG. 14, another exemplary embodiment of a remover 100 may include a connecting line 102 which is angled, circular, jig-saw configuration, etc. It is believed that including a connecting line 102 having a shape other than straight may increase the bond strength between the first edge 104 and second edge 106 of the remover 100 and prevent the edges from peeling away from each other. It is also believed that the connecting line 102 having a shape other than straight may prevent the edges from shearing with respect to each other when the remover 100 is used to remove a needle shield as previously described. The first edge 104 may have one or more nubs 108 and may have one or more pockets 110. The second edge 106 may have corresponding nubs 108 and pockets 110 such that the nubs from the first edge 104 are positioned within the pockets 110 of the second edge 106 and vice versa. In some embodiments, the nubs 108 and pockets 110 may be formed along the length of the connecting line 102. In other embodiments, the nubs 108 and pockets 110 may be formed along a portion of the connecting line 102 and the remaining portion of the connecting line 102 may be straight, angled, etc. The connecting line 102 may include any number of nubs 108 and pockets 110. In some embodiments, the nubs 108 and pockets 110 may be circular or arced. In other embodiments, the nubs 108 and pockets 110 may be straight.

It will be appreciated by those skilled in the art that changes could be made to the exemplary embodiments shown and described above without departing from the broad inventive concepts thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and various features of the disclosed embodiments may be combined. The words "right", "left", "lower" and "upper" designate directions in the drawings to which reference is made. The words "inwardly" and "outwardly" refer to directions toward and away from, respectively, the geometric center of the device. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the methods of the present invention do not rely on the particular order of steps set forth herein, the particular order of the steps should not be construed as limitation on the claims. Any claims directed to the methods of the present invention should not be limited to the performance of their steps in the order written, and one skilled in the art can readily appreciate that the steps may be varied and still remain within the spirit and scope of the present invention.

We claim:

1. An apparatus for removing a needle shield from a syringe, comprising:
   a remover having a proximal-to-distal axis, a body, and a first deflectable arm, the remover coupled to a syringe having a removable needle shield and configured to receive the removable needle shield,
   wherein the first deflectable arm includes a distal end coupled to the body and a proximal end axially spaced from an end of the body, the proximal end of the first deflectable arm configured to engage a barrel of a syringe when the remover is coupled to the syringe, the first deflectable arm configured to engage and apply a force to the needle shield when the remover is separated from the syringe, to thereby remove the needle shield from the syringe.

2. The apparatus of claim 1, wherein the body includes an opening and the first deflectable arm is positioned within the opening.

3. The apparatus of claim 1, further comprising a cap detachably coupled to an injector housing and attached to the remover.

4. The apparatus of claim 3, further comprising:
   a boss extending from the cap; and
   an aperture in the body configured to receive the boss to secure the remover to the cap.

5. The apparatus of claim 1, wherein the remover can rotate relative to the needle shield while engaged with the needle shield.

6. The apparatus of claim 1, further comprising:
   a second deflectable arm, the first deflectable arm and second deflectable arm moveable between a first configuration wherein the first deflectable arm and second deflectable arm are flexed radially outward and a second configuration wherein the first deflectable arm and second deflectable arm are aligned with the body.

7. The apparatus of claim 6, wherein the first deflectable arm and second deflectable arm are in the first configuration when the first deflectable arm and second deflectable arm are adjacent the syringe.

8. The apparatus of claim 7, wherein the first deflectable arm and second deflectable arm are in the second configuration when the first deflectable arm and second deflectable arm are adjacent a proximal end of the needle shield.

9. The apparatus of claim 3, further comprising a flange extending distally from the first deflectable arm, the flange engaging and applying a force to the proximal end of the needle shield when the cap is detached from the syringe.

10. The apparatus of claim 3, wherein the proximal end of the first deflectable arm is proximal to a proximal end of the cap.

11. The apparatus of claim 3, wherein the remover includes a central channel and the cap includes a projection extending proximally from a distal end of the cap and into the central channel when the remover is coupled to the cap.

12. The apparatus of claim 2, wherein the body includes a circumferential halo proximal to the opening.

13. The apparatus of claim 1, wherein a proximal end of the first deflectable arm is distal to a proximal end of the body.

14. The apparatus of claim 6, wherein the first deflectable arm and the second deflectable arm are in the first configuration when engaged with the barrel of the syringe.

15. The apparatus of claim 6, further comprising:
   a cap detachably coupled to an injector housing and attached to the remover,
   wherein the first deflectable arm and the second deflectable arm are in the first configuration when the coup cap is coupled to the injector housing.

16. The apparatus of claim 6, wherein the first deflectable arm is deflected from the second configuration to the first configuration as the needle shield is positioned within the remover.

17. The apparatus of claim 2, further comprising at least one additional opening in the body, wherein the opening and the at least one additional opening in the body are separated by struts.

18. The apparatus of claim 17, wherein a halo connects a proximal end of the struts.

* * * * *